United States Patent [19]

Renga et al.

[11] Patent Number: 4,979,978

[45] Date of Patent: Dec. 25, 1990

[54] HERBICIDAL 12H-DIBENZO[D,G][1,3]DIOXOCIN-6-CARBOXYLIC ACIDS

[75] Inventors: James M. Renga; Brian K. Riley, both of Santa Rosa; Patricia G. Ray; Michael G. Smith, both of Walnut Creek, all of Calif.

[73] Assignee: The Dow Chemical Company, Midland, Mich.

[21] Appl. No.: 366,826

[22] Filed: Jun. 15, 1989

[51] Int. Cl.$^5$ .................... A01N 43/24; C07D 321/12
[52] U.S. Cl. ........................................ 71/88; 549/346; 549/349
[58] Field of Search .................... 549/346, 349; 71/88; 514/450

[56] References Cited

U.S. PATENT DOCUMENTS

| | | | |
|---|---|---|---|
| 3,553,234 | 1/1971 | Johnson et al. | 549/349 |
| 3,836,543 | 9/1974 | Grisar | 549/349 |
| 3,931,173 | 1/1976 | Parker et al. | 549/349 |

OTHER PUBLICATIONS

J. M. Grisar et al., *J. Medicinal Chemistry,* 15, 1273–1278, 1972.
H. Linser, *Chemical Abstracts,* 53, 20313f, 1959.
J. L. Fults et al., *Chemical Abstracts,* 42, 1013f&g, 1948.

*Primary Examiner*—Richard L. Raymond
*Assistant Examiner*—Amelia A. Owens
*Attorney, Agent, or Firm*—D. Wendell Osborne

[57] ABSTRACT

12H-Dibenzo[d,g][1,3]dioxocin-6-carboxylic acids having at least one selected substituent in the 1-, 3-, 4-, 8-, 9-, or 11-position, such as 4-chloro-12H-dibenzo[d,g][1,3]dioxocin-6-carboxylic acid, and their agriculturally acceptable salts, esters, and amides, are useful for the control of undesirable vegetation.

28 Claims, No Drawings

HERBICIDAL 12H-DIBENZO[D,G][1,3]DIOXOCIN-6-CARBOXYLIC ACIDS

BACKGROUND OF THE INVENTION

The present invention relates to substituted dibenzo[d,g][1,3]dioxocin-6-carboxylic acids and to related compounds that are convertible to dibenzo[d,g][1,3]dioxocin-6-carboxylic acids in the environment or in plants and to the use of these compounds as herbicides.

Certain substituted dibenzo[d,g][1,3]dioxocin-6-carboxylic acids and certain of their corresponding esters and amides are known in the art and are reported to possess specific pharmacological utilities. See, for example, U.S. Pat. Nos. 3,931,173 and 3,553,234 and *J. Medicinal Chemistry*, 15, 1273–1278 (1972). Little else is known about this class of compounds.

The production of quality food and fiber is highly dependent on the availability of safe and effective herbicides to control unwanted vegetation. New compounds that are useful in this regard are continuously sought and when found, highly prized.

SUMMARY OF THE INVENTION

It has now been found that certain substituted dibenzo[d,g][1,3]dioxocin-6-carboxylic acids and the salts, esters and amides derived from these acids as well as other compounds which are chemically or biochemically converted to these acids in the environment or within plants are useful herbicides.

In particular, substituted dibenzo[d,g][1,3]-dioxocin-6-carboxylic acid compounds of Formula I

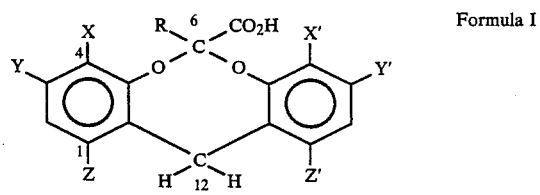

Formula I wherein
R represents H or $CH_3$ and
X, X', Y, Y', Z, and Z' each, independently represent H, F, Cl, Br, I, CN, $NO_2$, $CO_2H$, $NH_2$, $C_1$–$C_4$ alkyl, $C_1$–$C_4$ alkoxy, $C_1$–$C_4$ alkylthio, $C_1$–$C_4$ mono- or dialkylamino, ($C_1$–$C_3$ alkyl)carbonyl, or phenylcarbonyl, wherein each alkyl, alkoxy, and alkylthio group is optionally substituted with one or more compatible groups selected from $C_1$–$C_4$ alkoxy, $C_1$–$C_4$ alkylthio, F, Cl, Br, CN and phenyl and wherein each phenyl group is optionally substituted with up to 3 groups selected from F, Cl, Br, CN, $CF_3$, $C_1$–$C_4$ alkyl, and $C_1$–$C_4$ alkoxy: with the proviso that X, Y, Z, X', Y', and Z' do not all represent H; and the agriculturally acceptable salt, esters and amides thereof: and obtainable compounds which are oxidizable or hydrolyzable in plants or the environment to a dibenzo[d,g][1,3]dioxocin-6-carboxylic acid compound of Formula I are useful for the control of undesirable vegetation.

Compositions containing an herbicidally effective amount of a compound of Formula I in admixture with an agriculturally acceptable adjuvant or carrier are usually applied to the undesirable vegetation or the locus thereof in either preemergence or postemergence operations.

The compounds of Formula I wherein X', Y', and Z' each represent hydrogen and at least one of X, Y, and Z represents other than hydrogen are a preferred class as are the compounds of Formula I wherein R represents hydrogen.

Compounds of Formula I wherein one of X, Y, Z, X', Y', and Z' represents OH are useful intermediates for the preparation of other compounds of Formula I and are a part of the invention.

DETAILED DESCRIPTION OF THE INVENTION

The 12H-dibenzo[d,g][1,3]dioxocin-6-carboxylic acid compounds of Formula I wherein R, X, X', Y, Y', Z, and Z' are selected from among the substituents designated in the Summary of the Invention as well as the agriculturally acceptable salts, esters, and amides derived from these acids and compounds that are converted to these acids when applied as herbicides are compounds within the scope of the invention. The subject acids are characterized by the presence of a 12H-dibenzo[d,g][1,3]dioxocin ring system, a carboxylic acid moiety in the 6-position, the presence of at least one substituent other than hydrogen in the 1-, 3-, 4-, 8-, 9- or 11-position, and the absence of substituents other than hydrogen in the 2-, 10- and 12-positions.

The compounds of Formula I possess an asymmetric carbon atom at the 6-position and, therefore, can exist in two stereoisomeric forms. Both the R and the S isomers are described by Formula I and the present invention relates to each of these isomers independently as well as to all mixtures thereof.

The terms alkyl, alkenyl, alkoxy, and alkylthio as used herein include straight chain and branched chain isomers. Thus, typical alkyl groups are methyl, ethyl, 1-methylethyl, 1,1-dimethylethyl, propyl, 2-methylpropyl, 1-methylpropyl, and butyl.

Agriculturally acceptable salts, esters and amides are those salts, esters and amides of the carboxylic acid group(s) of Formula I which have a cation, OR, $NH_2$, NHR, or NRR moiety that is not itself significantly herbicidal to any crop being treated and not significantly deleterious to the applicator, the environment, or the ultimate user of any crop being treated.

Suitable cations include, for example, those derived from alkali or alkaline earth metals and those derived from ammonia and amines. Preferred cations include sodium, potassium, magnesium, and aminium cations of the formula

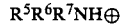

wherein $R^5$, $R^6$, and $R^7$ each, independently represents hydrogen or $C_1$–$C_{12}$ alkyl, $C_3$–$C_{12}$ cycloalkyl, or $C_3$–$C_{12}$ alkenyl, each of which is optionally substituted by one or more hydroxy, $C_1$–$C_8$ alkoxy, $C_1$–$C_8$ alkylthio or phenyl groups, provided that $R^5$, $R^6$, and $R^7$ are sterically compatible. Additionally, any two of $R^5$, $R^6$, and $R^7$ together may represent an aliphatic difunctional moiety containing 1 to 12 carbon atoms and up to two oxygen or sulfur atoms. Salts of the compounds of Formula 1 can be prepared by treatment of compounds of Formula I with a metal hydroxide, such as sodium hydroxide, potassium hydroxide, or magnesium hydroxide, or an amine, such as ammonia, triethylamine dimethylamine, hydroxyethylamine, bisallylamine, 2- butoxyethylamine, morpholine, cyclododecylamine, or benzylamine.

Suitable esters and amides include those wherein each R independently represents $C_1$-$C_8$ alkyl or $C_3$-$C_8$ alkenyl, each optionally substituted with up to 3 compatible groups selected from $C_1$-$C_4$ alkoxy, F, Cl, Br, and phenyl, or phenyl optionally substituted with up to 3 groups selected from F, Cl, Br, $CH_3$, or $CF_3$. $C_1$-$C_4$ Alkyl esters are generally preferred and methyl and butyl esters are often specifically preferred.

The nature of the substituents R, X, X', Y, Y', Z, and are sometimes preferred. Compounds wherein at least one of X and X' represents a designated substituent other than hydrogen are also sometimes preferred. Of the substituents. designated for X, X', Y, Y', Z, and Z', the following are often preferred: H, F, Cl, Br, $CH_3$, $OCH_3$, $SCH_3$, $CF_3$, and $OC_6H_5$. Compounds wherein X and X', Y and Y'. and Z and Z' are not simultaneously the same are generally preferred. Hydrogen is a preferred R substituent.

The compounds of Table I are illustrative of the compounds of the invention.

TABLE I

Representative Compounds of Formula I

| Cpd No. | X | Y | Z | X' | Y' | Z' | R | Form of Acid |
|---|---|---|---|---|---|---|---|---|
| 1 | $CH_3$ | H | H | H | H | H | H | acid |
| 2 | $CH_3$ | H | H | H | H | H | H | $CH_3$ ester |
| 3 | H | H | $CH_3$ | H | H | H | H | acid |
| 4 | H | H | $CH_3$ | H | H | H | H | $CH_3$ ester |
| 5 | Cl | H | H | H | H | H | H | acid |
| 6 | Cl | H | H | H | H | H | H | $CH_3$ ester |
| 7 | F | H | H | H | H | H | H | acid |
| 8 | F | H | H | H | H | H | H | $CH_3$ ester |
| 9 | Br | H | H | H | H | H | H | acid |
| 10 | Br | H | H | H | H | H | H | $CH_3$ ester |
| 11 | H | H | F | H | H | H | H | acid |
| 12 | H | H | F | H | H | H | H | $CH_3$ ester |
| 13 | H | $OCH_3$ | H | H | H | H | H | acid |
| 14 | H | $OCH_3$ | H | H | H | H | H | $CH_3$ ester |
| 15 | $SCH_3$ | H | H | H | H | H | H | acid |
| 16 | $SCH_3$ | H | H | H | H | H | H | $CH_3$ ester |
| 17 | $OCH_3$ | H | H | H | H | H | H | acid |
| 18 | $OCH_3$ | H | H | H | H | H | H | $CH_3$ ester |
| 19 | Cl | H | H | $OCH_3$ | H | H | H | acid |
| 20 | Cl | H | H | $OCH_3$ | H | H | H | $CH_3$ ester |
| 21 | Cl | H | $CH_3$ | H | H | H | H | acid |
| 22 | Cl | H | $CH_3$ | H | H | H | H | $CH_3$ ester |
| 23 | $OC_2H_5$ | H | H | H | H | H | H | $CH_3$ ester |
| 24 | $OCH_2C_6H_5$ | H | H | H | H | H | H | $CH_3$ ester |
| 25 | $OCH_2CH$ | H | H | H | H | H | H | $CH_3$ ester |
| 26 | $CO_2CH_3$ | H | H | H | H | H | H | $CH_3$ ester |
| 27 | H | I | H | H | $OC_4H_9$ | H | $CH_3$ | di-$CH_3$ amide |
| 28 | Cl | Cl | H | H | $CF_3$ | $SC_3H_7$ | $CH_3$ | potassium salt |
| 29 | $N(CH_3)_2$ | H | CN | $C_3H_7$ | H | $CH_3$ | H | $C_8H_{17}$ ester |
| 30 | Br | H | $OCH_3$ | H | $OCH_3$ | Cl | $CH_3$ | $CH_3OCH_2CH(CH_3)_2$ ester |
| 31 | $NO_2$ | $CH_3$ | $CH_3$ | $SCF_3$ | F | F | $CH_3$ | $C_2H_5OC_2H_4$ amide |
| 32 | $OCF_2CF_2H$ | H | $CH_3$ | H | H | I | $CH_3$ | $(C_2H_5)_3NH^+$ salt |
| 33 | Cl | Cl | Cl | H | H | H | H | $NH_2$ amide |
| 34 | H | $NO_2$ | H | H | H | CN | $CH_3$ | $C_4H_9$ ester |
| 35 | $CH_3$ | $CH_3$ | Br | H | H | Br | H | $HO(CH_2)_2NH_3^+$ salt |
| 36 | I | I | H | I | I | H | $CH_3$ | $NH_4^+$ salt |
| 37 | Cl | H | H | Cl | H | H | H | $CH_3CHCHCH_2$ ester |
| 38 | $CH_3$ | H | H | $CH_3$ | H | H | H | $C_6H_5CH_2$ ester |
| 39 | Cl | H | $CF_3$ | Cl | H | $CF_3$ | H | cyclo-$C_6H_{11}$ ester |
| 40 | $CH_3$ | H | $CH_3$ | $CH_3$ | H | $CH_3$ | H | $CHCCH_2$ ester |
| 41 | CN | H | H | H | H | H | H | Acid |
| 42 | CN | H | H | H | H | H | H | $CH_3$ ester |
| 43 | $CF_3$ | H | H | H | H | H | H | Acid |
| 44 | $CF_3$ | H | H | H | H | H | H | $CH_3$ ester |
| 45 | $OCH_3$ | $OCH_3$ | H | H | H | H | H | $CH_3$ ester |
| 46 | H | $CH_3$ | H | H | H | H | H | $CH_3$ ester |
| 47 | H | Cl | H | H | H | H | H | Acid |
| 48 | H | Br | H | H | H | H | H | Acid |
| 49 | Cl | H | H | H | $OCH_3$ | H | H | $CH_3$ ester |
| 50 | H | H | CN | H | H | H | H | Acid |
| 51 | H | H | Br | H | H | H | H | $CH_3$ ester |

Z' within the described limits does not appear to be critical to the general utility of the compounds, but it is a factor in determining the degree of herbicidal activity and the selectivity of the herbicidal action of these compounds with respect to weeds controlled and crops not affected. Consequently, some of the compounds are preferred. With respect to the ring substituents X, X', Y, Y', Z, and Z', compounds wherein X', Y' and Z' all represent hydrogen and at least one of X, Y, and Z represents a designated substituent other than hydrogen Compounds which are obtainable employing the teachings herein, the teachings and suggestions in the art, and ordinary skill in the art and which degrade in the environment or within plants to a compound of Formula I will have utilities similar to the compounds of Formula I and the use of such compounds is within the scope of the present invention. Many such compounds can be envisioned. Thus, those compounds which are readily oxidized and/or hydrolyzed in the environment or within a plant system to a compound of Formula I, such as, for example, the 6-hydroxymethyl, 6-aminomethyl, 6-formyl, 6-(2-carboxyethyl), 6-(5-chloro-2-pentenyl), 6-cyano, 6-(2-dioxolanyl), and many other derivatives have approximately the same utility as the compound to which they degrade. The art is replete with other functional groups which are degradable to carboxylic acids, and accordingly, when any of these functional groups is present in place of the carboxylic acid moiety in the 6-position of a compound of Formula I, a useful herbicide is obtained.

The compounds of the present invention can be prepared in a number of ways. The most general method involves the condensation of a bisphenol compound of Formula II, wherein X, X', Y, Y', Z, and Z' are as defined in the Summary of the Invention, with a 2,2-dihaloalkanoic acid of Formula III, wherein R represents hydrogen or methyl and G denotes chloro or bromo: or with an ester or amide of such a 2,2-dihaloalkanoic acid. Dichloroacetic acid is preferred.

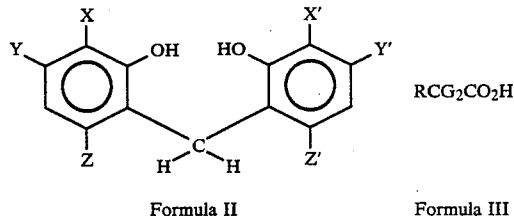

Formula II          Formula III

The process can be carried out essentially as described for related compounds in U.S. Pat. Nos. 3,553,234 and 3,931,173, and *J. Med. Chem.*, 15, 1273–1278 (1972), the appropriate portions of which are hereby incorporated by reference. It is often convenient to reflux a mixture of a compound of Formula II and a compound of Formula III (or an ester or amide thereof) in a solvent with potassium carbonate and a catalytic amount of potassium iodide for a few days. 2-Propanol is a preferred solvent.

It is generally preferred to do the above condensation with an acid of Formula III and, if desired, to subsequently convert the compound of Formula I (acid form) obtained to an agriculturally acceptable salt, ester, or amide using standard methods well known to those of ordinary skill in the art. It is sometimes preferred to choose the acid, ester or amide of a compound of Formula III which corresponds to a desired acid, ester or amide of the compound of Formula I to be prepared. In this way the subsequent interconversion of these functionalities to obtain the desired derivative can be avoided.

Alternately, the cyclization can be accomplished by condensation of a bisphenol of Formula II with diethyl dibromomalonate and base. The desired compound of Formula I can be obtained after hydrolysis and decarboxylation of the product prepared, using standard conditions for such reactions. This condensation requires less drastic conditions than the usual method and is valuable for compounds having substituents that are unstable in base, such as trifluoromethyl.

A variety of compounds of Formula 11, wherein X, X', Y, Y', Z, and Z' are as defined in the Summary of the Invention, are known in the art. These and other compounds of Formula II can be prepared in a variety of ways. For example, compounds of Formula II can be prepared by condensing an appropriate compound of Formula IV wherein R" represents methyl or methoxymethyl and W represents hydrogen or bromo with an appropriate compound of Formula V wherein R' represents methyl, methoxymethyl, or hydrogen with an alkyl lithium compound, such as butyl lithium, and subsequently reducing and dealkylating the bis(substituted-phenyl)methanol of Formula VI obtained.

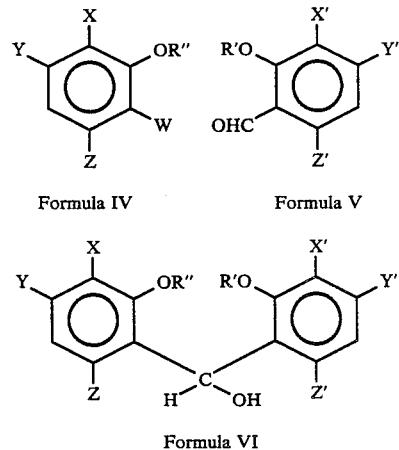

Formula IV          Formula V

Formula VI

R" is often preferably methoxymethyl and R' is often preferably methyl. W is usually preferably hydrogen unless X is hydrogen or bromo in which case bromo is usually preferable. The condensation can be carried out by first lithiating the compound of Formula IV with an alkyl lithium at about 0° C. in an ether type solvent, such as tetrahydrofuran, in the presence of a complexing agent, such as tetramethylethylenediamine, and then allowing the lithium compound formed to react with the substituted benzaldehyde compound of Formula V under similar conditions. The compound of Formula VI formed can be recovered by adding a saturated aqueous solution of ammonium chloride and extracting with ether.

A variety of methods exist for reducing and dealkylating the compounds of Formula VI to compounds of Formula II. It has been found convenient to first reduce the bis(substituted-phenyl)methanol of Formula VI to the corresponding bis(substituted-phenyl)methane with a trialkylsilane and trifluoroacetic acid. Typically, the compound of Formula VI is treated with these reagents in a solvent, such as methylene chloride, at ambient temperature. The product can be recovered by quenching the reaction mixture with saturated aqueous sodium bicarbonate and extracting with ether. The bis(substituted-phenyl)methane thus obtained can be dealkylated (have the R' and R" alkyl groups removed) by most general methods for such reactions. Sometimes, methoxymethyl groups are removed incidentally in the trialkylsilane reduction process. Typically, methoxymethyl groups can be removed by allowing the compounds to react with p-toluenesulfonic acid in refluxing methanol or by treatment with bromodiethylborane. Methyl groups can be removed by reaction with boron tribromide. In general, the methoxy containing compound is allowed to react with boron tribromide in a solvent, such as methylene chloride, at ambient temperature to effect the reaction. The resulting compound of Formula II can be recovered by conventional means, such as extraction into aqueous alkali and then adding acid.

A large number of the starting material compounds of Formulas IV and V are known in the art or can be made by methods known in the art. Ether compounds of Formula IV are readily prepared from the corresponding phenols of Formula VII by conventional methods.

Alternately, many of the compounds of Formula II can be prepared by condensation of a compound of Formula VII with a compound of Formula VIII using a Grignard reagent, such as ethyl magnesium bromide, in excess. Typically, the condensation is effected by combining the reagents in ether, replacing the ether with benzene after a short period, and heating the latter mixture at reflux for several hours. The compound of Formula II is recovered by conventional techniques for Grignard reactions. A large number of the starting material compounds of Formulas VII and VIII are known in the art or can be made by methods known in the art.

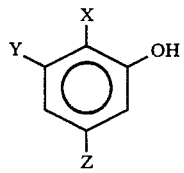
Formula VII

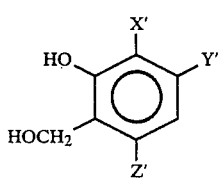
Formula VIII

Other methods exist for the preparation of compounds of Formula II. For example, many dihydroxybenzophenones of Formula IX are known in the art or can be made by methods known in the art and many of these can be reduced to compounds of Formula II.

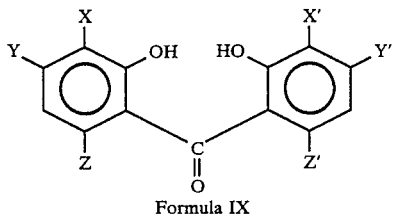
Formula IX

Reducing agents such as hydrogen in the presence of a catalyst, such as palladium on carbon, and hydrazine in the presence of a base can be employed.

The choice of a method to use in the preparation of the desired compound of Formula II will depend on the availability of starting materials, the sensitivity of the substituents to the reaction conditions that will be employed in subsequent reactions, and the possibility of isomer formation which would make recovery of the desired product difficult. Protecting groups can be employed in the process and subsequently removed as is known in the art.

It is not always necessary to prepare a compound of Formula II to obtain the corresponding compound of Formula I. It is often possible and desirable to convert one compound of Formula I (or a related compound with a substituent pattern not covered by Formula 1) to another compound of Formula 1 using convention chemical methods. Thus, for example, a 1,1-dimethylethyl group can be used as a protecting group and removed by treatment with aluminum chloride, a bromo or iodo substituent can be removed with a reducing agent or replaced by other groups by nucleophilic displacement, such as with cuprous cyanide, a nitro group can be reduced to an amino group, a trialkylsilyl group can be replaced by bromo or iodo, and a methoxy group can be converted to a hydroxy group with an alkanethiol and base. An hydroxy group can further be alkylated by known methods to alkoxy groups, including substituted alkoxy groups as defined in the Summary of the Invention. Such transformations are well known to those in the art.

It is further possible to prepare compounds of Formula I from compounds of Formula IX by first condensing the latter with a compound of Formula III in the same manner employed in the reaction of compounds of Formula 11 with compounds of Formula III and then reducing the 12-oxo analog of the compound of Formula I obtained. In typical operations, the 12-oxo compound is reduced at ambient temperature with hydrogen in a solvent, such as methanol, using a catalyst, such as palladium on carbon.

Compounds of Formula I wherein R represents methyl are usually best prepared by methylation of a compound of Formula I wherein R represents hydrogen. In typical operations a compound of Formula I wherein R represents hydrogen is added dropwise with stirring to a solution of an alkyl lithium compound, such as butyl lithium, and diisopropylamine in a solvent, such as tetrahydrofuran, while cooling with dry-ice and acetone to about −78° C. and after a few minutes adding excess methyl iodide. The 6-methyl compound can be recovered be conventional means, for example, by adding dilute aqueous hydrochloric acid and then extracting with ether.

The compounds of the present invention can be used directly as herbicides, but it is generally preferable to first prepare a herbicidal composition containing one or more of the compounds in combination with an agriculturally acceptable adjuvant or carrier. Suitable adjuvants or carriers should not be phytotoxic to valuable crops, particularly at the concentrations employed in applying the compositions for selective weed control in the presence of crops, and should not react chemically with compounds of Formula I or other composition ingredients. Such mixtures can be designed for application directly to plants or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or non-ionic in character and can be employed as emulsifying agents, wetting agents, suspending agents, or for other purposes. Typical surface active agents include salts of alkyl sulfates, such as diethanol ammonium lauryl sulfate: alkylarylsulfonate salts, such as calcium dodecylbenzenesulfonate: alkylphenol-alkylene oxide addition products, such as nonylphenol-C18 ethoxylate: alcohol-alkylene oxide addition products, such as tridecyl alcohol-C16 ethoxylate: soaps, such as sodium stearate; alkylnaphthalenesulfonate salts, such as sodium dibutylnaphthalenesulfonate: dialkyl esters of sulfosuccinate salts, such as sodium di(2-ethylhexyl) sulfosuccinate; sorbitol esters, such as sorbitol oleate; quaternary amines, such as lauryl trimethylammonium chloride: polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include anti-foam agents, compatibilizing agents, sequestering agents, UV absorbers, neutralizing agents and buffers, corrosion inhibitors, dyes, odorant, penetration aids, spreading agents, sticking agents, dispersing agents, thickening agents, freeze point depressants, antimicrobial agents, and the like. The addition of crop oil and crop oil concentrates is typical. The compositions can also contain other compatible components, for example, other herbicides, plant growth regulants, fungicides, insecticides, and the like and can be formulated with solid, particulate fertilizer carriers such as ammonium nitrate, urea and the like or with liquid fertilizers.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to plants or their locus generally contain about 0.001 to about 5 weight percent active ingredient and preferably contain about 0.01 to about 1.0 percent.

The present compositions can be applied by the use of conventional ground or aerial dusters and sprayers, by addition to irrigation water, and by other conventional means known to those skilled in the art.

General herbicide action is usually observed for compounds of Formula I at rates of about 0.5 to about 10 lb/acre. Selective herbicidal action wherein undesirable vegetation is controlled in the presence of desirable crop plants is typically observed with some of the compounds at about 0.1 to about 4 lb/acre. For example, broadleaf weed can often be controlled in the presence of grassy crops, such as corn, wheat, barley, and rice with compounds of the present invention. An appropriate rate for each crop, compound and circumstance can be determined by simple range finding tests using the teachings herein.

The term "herbicide" is used herein to mean an active ingredient which controls or adversely modifies growth of plants. By "vegetation controlling" or "herbicidally effective" amount is meant an amount of active ingredient which causes an adversely modifying effect and includes deviations from natural development, killing, regulation, desiccation, retardation, and the like. The terms "plants" and "weeds" are meant to include germinant seeds, emerging seedlings and established vegetation. "Undesirable vegetation" is plant life present in a place where it is not wanted.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, and the like, as well as the amount of chemical applied These and other factors can be adjusted as is known in the art to promote selective herbicidal action.

EXAMPLES

Example 1

Preparation of (3-Methyl-2-hydroxyphenyl)-(2-hydroxyphenyl)methane

2-Hydroxybenzyl alcohol (18.6 g, 0.15 mol) and o-cresol (16.2 g, 0.15 mol) were dissolved in 150 ml of ether in a flask and a dry nitrogen atmosphere established. Ethyl magnesium bromide (100 ml of 3M solution in ether, 0.30 mol) was added dropwise with stirring. The ether was removed by evaporation under reduced pressure and 450 ml of benzene added. The resulting mixture was heated at reflux with stirring for 20 hours and then allowed to cool. Saturated aqueous ammonium chloride solution was added and the mixture extracted with 2-500 ml portions of ether. The combined ether extracts were dried over magnesium sulfate and the ether then removed by evaporation. The residue was chromatographed on a silica gel column eluting with an 80:20 mixture of hexane and ethyl acetate and dried in a vacuum oven at 100° C. to obtain 7.6 g (24 percent of theory) of (3-methyl-2-hydroxyphenyl) (2-hydroxyphenyl)methane as an oil.

Example 2

Preparation of 4-Methyl-12H-dibenzo-[d,g][1,3]dioxocin-6-carboxylic Acid (3-Methyl-2-hydroxyphenyl)(2-hydroxyphenyl)methane (3.4 g, 16 mmol), potassium carbonate (8.84 g, 64 mmol), potassium iodide (0.53 g, 3.2 mmol), dichloroacetic acid (2.06 g, 16 mmol), and 65 ml of 2-propanol were heated at reflux with stirring under nitrogen for 30 hours. Another 2.05 g (16 mmol) of dichloroacetic acid was added and heating at reflux continued for 60 hours. The 2-propanol was then removed by evaporation under reduced pressure and the residue was diluted with distilled water and acidified with 2N hydrochloric acid. This mixture was extracted with ether and the ether extract was dried over magnesium sulfate and evaporated under reduced pressure to obtain 1.8 g (42 percent of theory) of the title compound as a solid residue. A purified sample melting at 171° C. was obtained by recrystallization from a mixture of methylcyclohexane and acetone. The proton nmr spectrum was consistent with the assigned structure.

Elemental Analysis:

Calc. for $C_{16}H_{14}O_4$: % C, 71.1: % H, 5.22.
Found: % C, 71.9: % H, 5.94.

The following were prepared analogously and found to have the assigned structures by proton nmr spectra and in most cases elemental analyses:

4-Methylthio-12H-dibenzo[d,g][1,3]dioxocin-6-carboxylic acid, a solid, m.p., 58°–61° C.;
4-Bromo-12H-dibenzo[d,g][1,3]dioxocin-6-carboxylic acid, a solid, m.p., 140°–149° C.;
4-Fluoro-12H-dibenzo[d,g][1,3]dioxocin-6-carboxylic acid, a solid, m.p., 156°–159° C.;
1-Fluoro-4-methyl-12H-dibenzo[d,g][1,3]dioxocin-6-carboxylic acid, a white solid, m.p., 187°–188° C.;
4-Chloro-8-methoxy-12H-dibenzo[d,g][1,3]dioxocin-6-carboxylic acid, a solid, m.p., 169°–170° C.:
3-Methyl-12H-dibenzo[d,g][1,3]dioxocin-6-carboxylic acid, a white powder, m.p., 143°–147° C.:
1-Bromo-12H-dibenzo[d,g][1,3]dioxocin-6-carboxylic acid, a white powder, m.p., 196°–198° C.:
3-Bromo-12H-dibenzo[d,g][1,3]dioxocin-6-carboxylic acid, a white powder, m.p., 167°–170° C.;
3-Cyano-12H-dibenzo[d,g][1,3]dioxocin-6-carboxylic acid, a white powder, m.p., 176°–180° C.:
1-Cyano-12H-dibenzo[d,g][1,3]dioxocin-6-carboxylic acid, a white powder, m.p., 193°–194° C.:
4-Chloro-3-methoxy-12H-dibenzo[d,g][1,3]dioxocin-6-carboxylic acid, a beige powder, m.p., 63°–70° C.:
8-Chloro-3-methoxy-12H-dibenzo[d,g][1,3]dioxocin-6-carboxylic acid, a beige solid;
4-Chloro-1-methyl-12H-dibenzo[d,g][1,3]dioxocin-6-carboxylic acid, a white solid, m.p., 213°–214° C.: and
3,4-Dimethoxy-12H-dibenzo[d,g][1,3]dioxocin-6-carboxylic acid, a white solid.

Example 3

Preparation of Methyl 4-Methyl-12H-dibenzo[d,g][1,3]dioxocin-6-carboxylate

4-Methyl-12H-dibenzo-[d,g][1,3]dioxocin-6-carboxylic acid from Example 1 (1.8 g, 6.6 mmol) was mixed with 75 ml of methanol and 5 g of Dowex TM sulfonic acid resin and the mixture heated at reflux for 16 hours. The mixture was allowed to cool, the resin removed by filtration, and the volatile components removed by evaporation under reduced pressure The residue was taken up in 150 ml of ether and the solution extracted with saturated aqueous sodium bicarbonate and dried over magnesium sulfate. The volatiles were removed by evaporation under reduced pressure and the light yellow residual solid, which amounted to 1.29 g, was recrystallized from ethanol to obtain 0.77 g (41 percent of theory) of the title compound as a solid melting at 104°–105° C. The proton nmr spectrum was consistent with the assigned structure.

Elemental Analysis:

Calc. for $C_{17}H_{16}O_4$: % C, 71.8; % H, 5.67.
Found: % C, 72.0; % H, 5.65.

The following were prepared analogously and found to have the assigned structures by elemental analyses and proton nmr spectra:

Methyl 4-methylthio-12H-dibenzo[d,g][1,3]dioxocin-6-carboxylate, a white solid, m.p., 109°–110° C.;
Methyl 4-bromo-12H-dibenzo[d,g][1,3]dioxocin-6-carboxylate, a solid, m.p., 102°–103° C.:
Methyl 4-fluoro-12H-dibenzo[d,g][1,3]dioxocin-6-carboxylate, a solid, m.p., 105°–106° C.;
Methyl 1-fluoro-4-methyl-12H-dibenzo[d,g][1,3]-dioxocin-6-carboxylate, a white solid, m.p., 131°–132° C.;
Methyl 4,8-dichloro-12H-dibenzo[d,g][1,3]dioxocin-6-carboxylate, a solid, m.p., 113°–114° C.;
Methyl 4-chloro-8-methoxy-12H-dibenzo[d,g][1,3]-dioxocin-6-carboxylate, a solid, m.p., 143°–144° C.;
Methyl 4-chloro-1-methyl-12H-dibenzo[d,g][1,3]-dioxocin-6-carboxylate, a white solid, m.p., 143° C.;
Methyl 3,4-dimethoxy-12H-dibenzo[d,g][1,3]dioxocin-6-carboxylate, a white solid, m.p., 135°–137° C.;
Methyl 3-methyl-12H-dibenzo[d,g][1,3]dioxocin-6-carboxylate, a white solid, m.p., 116°–118° C.;
Methyl 1-bromo-12H-dibenzo[d,g][1,3]dioxocin-6-carboxylate, a white powder, m.p. 127°–128° C.;
Methyl 3-bromo-12H-dibenzo[d,g][1,3]dioxocin-6-carboxylate, a white powder, m.p., 121°–124° C.;
Methyl 3-cyano-12H-dibenzo[d,g][1,3]dioxocin-6-carboxylate, a white powder, m.p., 161°–162° C.;
Methyl 1-cyano-12H-dibenzo[d,g][1,3]dioxocin-6-carboxylate, a beige powder, m.p., 147°–149° C.:
Methyl 4-chloro-3-methoxy-12H-dibenzo[d,g][1,3]-dioxocin-6-carboxylate, a white powder, m.p., 162°–164° C.;
Methyl 8-chloro-3-methoxy-12H-dibenzo[d,g][1,3]-dioxocin-6-carboxylate, white crystals, m.p., 161°–162° C.:
Methyl 3-chloro-12H-dibenzo[d,g][1,3]dioxocin-6-carboxylate, a white solid, m.p., 100°–101° C.:
Methyl 4-trifluoromethyl-12H-dibenzo[d,g][1,3]dioxocin-6-carboxylate, a white solid, m.p., 94°–99° C.; and
Methyl 4-cyano-12H-dibenzo[d,g][1,3]dioxocin-6-carboxylate, a beige powder, m.p., 139°–142° C.

Example 4

Preparation of (3-t-Butyl-2-hydroxy-5-methylphenyl)(2-hydroxyphenyl)methane

The procedure of Example 1 was followed. 2-t-Butyl-4-methylphenol (24.6 g, 0.15 mol) was used in place of the o-cresol and the product was purified by devolatilization at 85° C. and 2mm pressure in a Kugelrohr still and then preparative liquid chromatography eluting with a 10:90 mixture of acetone and hexane. The title compound was obtained as an oil and amounted to 4.34 g (11 percent of theory). The proton nmr spectrum was consistent with the assigned structure.

Elemental Analysis:

Calc. for $C_{18}H_{22}O_2$: % C, 80.0: % H, 8.20.
Found: % C, 80.0; % H, 8.18.

Example 5

Preparation of (2-Hydroxy-5-methylphenyl)-(2-hydroxyphenyl)methane (3-t-Butyl-2-hydroxy-5-methylphenyl)-(2-hydroxyphenyl)methane (4.34 g, 16 mmol) was combined with 3.2 g (24 mmol) of aluminum chloride and 100 ml of benzene and the mixture heated at reflux with stirring for 24 hours. It was then allowed to cool and was poured onto an ice-water mixture. The organic phase was collected and extracted with water and then 1N potassium hydroxide. The alkaline extract was acidified and then extracted with ether. The ether extract was dried with magnesium sulfate and the volatiles removed by evaporation under reduced pressure to obtain 1.66 g (48 percent of theory) of the title compound as an oil. The proton nmr spectrum was consistent with the assigned structure.

Example 6

Preparation of 1-Methyl-12H-dibenzo[d,g][1,3]dioxocin-6-carboxylic Acid (2-Hydroxy-5-methylphenyl)(2-hydroxyphenyl)methane (1.66 g, 7.7 mmol) was combined with 2.07 g (15 mmol) of potassium carbonate, 0.56 g (3.4 mmol) of potassium iodide, 0.99 g (7.7 mmol) of dichloroacetic acid and 50 ml of 2-propanol and the mixture heated at reflux with stirring for 24 hours. Another 7.7 mmol of dichloroacetic acid was added and the reaction continued for 2 days. The volatiles were removed by evaporation under reduced pressure and water added. The mixture was acidified with 1N hydrochloric acid and extracted with ether. The ether extract was dried over magnesium sulfate and the ether removed by evaporation under reduced pressure to obtain 2.63 g of the title compound in impure form as a brown oil. The proton nmr spectrum was consistent with the presence of desired product. A sample of the title compound prepared by hydrolysis of the product of Example 7 with potassium hydroxide in an aqueous methanol mixture at ambient temperature overnight melted at 61° C. and had a proton nmr spectrum consistent with the assigned structure.

Elemental Analysis:

Calc. for $C_{16}H_{14}O_4$: % C, 71.1: % H, 5.22.
Found: % C, 70.2: % H, 5.31.

Example 7

Preparation of Methyl 1-Methyl-12H-dibenzo[d,g][1,3]dioxocin-6-carboxylate

1-Methyl-12H-dibenzo[d,g][1,3]dioxocin-6-carboxylic acid from Example 6 (2.63 g of impure, 12.3 mmol) was mixed with 150 ml of methanol and 10 g of Dowex ™ sulfonic acid resin and the mixture heated at reflux overnight. The mixture was allowed to cool, the resin removed by filtration, and the volatile components removed by evaporation under reduced pressure. The residue was taken up in ether and the solution extracted with saturated aqueous sodium bicarbonate and dried over magnesium sulfate. The volatiles were removed by evaporation under reduced pressure and the brown oil residue was further devolatilized in a Kugelrohr still.

The residue was purified by preparative liquid chromatography eluting with a 10:90 mixture of acetone and hexane to obtain 0.69 g (32 percent of theory) of the title compound as a light colored solid melting at 93°-95° C. The proton nmr spectrum was consistent with the assigned structure.

Elemental Analysis:

Calc. for $C_{17}H_{16}O_4$: % C, 71.8: % H, 5.67.
Found: % C, 71.2; % H, 5.73.

Example 8

Preparation of 1-Chloro-2-methoxymethoxybenzene

2-Chlorophenol (96.4 g, 0.75 mol), dimethoxymethane (257.9 g, 3.39 mol) and 750 mg of p-toluenesulfonic acid were dissolved in 1.5 L of methylene chloride and the mixture heated at reflux with stirring under nitrogen for 72 hours in a flask equipped with a Soxhlet extraction apparatus containing 400 g of 3A molecular sieves. The mixture was allowed to cool and 3 ml of triethylamine was added. The mixture was then extracted with 2N sodium hydroxide and the organic phase was dried over magnesium sulfate. Evaporation of the volatiles under reduced pressure left 66.9 g of crude 1-chloro-2-methoxymethoxybenzene as a residue. This was distilled and the fraction boiling at 94° C. and 6.5 mm pressure was collected to obtain 51.3 g (40 percent of theory) of purified product. The proton nmr spectrum was consistent with the assigned structure.

Example 8

Preparation of (3-Chloro-2-methoxymethoxy-phenyl)(2-methoxyphenyl)methanol

A solution containing 69 ml of 1.6 N butyl lithium (0.11 mol) and 12.78 g (0.11 mol) of tetramethylethylenediamine was prepared under nitrogen and cooled to 0° C. To this was added, with stirring and cooling at 0° C., 16.83 g (0.098 mol) of 1-chloro-2-methoxymethoxybenzene. After 3 hours 13.34 g (0.098 mol) of o-anisaldehyde in 40 ml of anhydrous tetrahydrofuran was added slowly at 0°-5° C. and allowed to react. The product was then poured into a mixture of ice and saturated aqueous ammonium chloride and the resulting mixture was extracted with ether. The ether extract was dried over magnesium sulfate and then the volatiles were removed by evaporation under reduced pressure to obtain 29.3 g of crude title compound as a yellow solid. This was purified by preparative liquid chromatography eluting with a 10:90 mixture of acetone and hexane to obtain 21.1 g (70 percent of theory) of the title compound as a white solid melting at 89°-90° C. The proton nmr spectrum was consistent with the assigned structure.

Elemental Analysis:

Calc. for $C_{16}H_{17}ClO_4$: % C, 62.2; % H, 5.55.
Found: % C, 62.2; % H, 5.54.

Example 9

Preparation of (3-Chloro-2-hydroxyphenyl)-(2-methoxyphenyl)methane (3-Chloro-2-methoxymethoxyphenyl)(2-methoxyphenyl)methanol (15.27 g, 49 mmol) was combined with 15.97 g (100 mmol) of triethylsilane in 150 ml of methylene chloride and to this was added at ambient temperature with stirring under nitrogen 14.8 g (130 mmol) of trifluoroacetic acid. The mixture was stirred for 4 hours and was then poured into saturated aqueous sodium bicarbonate. Additional methylene chloride was added and the organic phase was recovered, dried over magnesium sulfate, and concentrated by evaporation under reduced pressure. The residue was purified by preparative liquid chromatography eluting with a 1:99 mixture of acetone and hexane to obtain 3.98 g (33 percent of theory) of the title compound. The proton nmr spectrum was consistent with the assigned structure.

Example 10

Preparation of
(3-Chloro-2-hydroxyphenyl)-(2-hydroxyphenyl)methane (3-Chloro-2-hydroxyphenyl)(2-methoxyphenyl)methane (3.98 g, 16 mmol) was dissolved in 100 ml of methylene chloride and 24 ml of 1M boron tribromide in methylene chloride (24 mmol) was added under nitrogen with stirring at ambient temperature. The mixture was allowed to react for 4 hours and then 100 ml of water was added slowly at ambient temperature. The organic layer was recovered and extracted with 2 N sodium hydroxide. The alkaline extract was acidified with 6 N hydrochloric acid and extracted with ether. The ether extract was dried over magnesium sulfate and concentrated by evaporation under reduced pressure to obtain 2.7 g (72 percent of theory) of the title compound. The proton nmr spectrum was consistent with the assigned structure.

Example 11

Preparation of
4-Chloro-12H-dibenzo-[d,g][1,3]dioxocin-6-carboxylic Acid

The procedure of Example 2 was followed using 2.7 g of (3-chloro-2-hydroxyphenyl)(2-hydroxyphenyl)methane as the bisphenol. The crude product amounted to 6.43 g. The proton nmr spectrum indicated the title compound was present. A purified sample obtained by hydrolysis of the product of Example 12 with potassium hydroxide in aqueous methanol at ambient temperature was a white solid melting at 153.5°–154.5° C. The proton nmr spectrum was consistent with the assigned structure.

Elemental Analysis:

Calc. for $C_{15}H_{11}ClO_4$: % C, 62.0; % H, 3.81.
Found: % C, 61.8; % H, 3.93.

Example 12

Preparation of Methyl
4-Chloro-12H-dibenzo[d,g][1.3]dioxocin-6-carboxylate

4-Chloro-12H-dibenzo[d,g][1,3]dioxocin-6-carboxylic acid (6.24 g of impure from Ex. 11, 22 mmol) was treated with methanol using the procedure of Examples 3 and 7. The crude product was purified by preparative liquid chromatography eluting with a 10:90 mixture of acetone and hexane to obtain 1.0 g (15 percent of theory) of the title compound as a solid melting at 107°–108° C. The proton nmr spectrum was consistent with the assigned structure.

Elemental Analysis:

Calc. for $C_{16}H_{13}ClO_4$: % C, 63.1; % H, 4.30.
Found: % C, 63.3: % H, 4.28.

Example 13

Preparation of
(2-Methoxymethoxyphenyl)-(2-hydroxy-3-methoxyphenyl)methanol

A 1.6 M solution of butyl lithium (90.6 ml, 0.145 mol) was placed in a flask and blanketed with nitrogen and to this was added with stirring, while maintaining the temperature at 25°–30° C., 16.85 g, (0.145 mol) of tetramethylethylenediamine. The mixture was then cooled to 0° C. and 20.0 g (0.145 mol) of methoxymethoxybenzene was added with stirring and allowed to react for 2 hours after which 10.0 g (0.066 mol) of 2-hydroxy-3-methoxybenzaldehyde was added under the same conditions. The mixture was allowed to react for a few minutes and was then poured into a mixture of ice and saturated aqueous ammonium chloride. The solid that formed, which was insoluble in ether, was collected by filtration to obtain 15.5 g (81 percent of theory) of the title compound. The proton nmr spectrum was consistent with the assigned structure.

Example 14

Preparation of
(2-Methoxymethoxyphenyl)-(2-hydroxy-3-methoxyphenyl)methane (2-Methoxymethoxyphenyl)(2-hydroxy-3-methoxyphenyl)methanol (15.54 g, 54 mmol) and triethylsilane (7.53 g, 0.064 mol) were dissolved in 150 ml of methylene chloride and the solution cooled to 0° C. and blanketed with nitrogen. A solution of 7.39 g (64.8 mmol) of trifluoroacetic acid in 70 ml of methylene chloride was added with stirring and cooling and the mixture was allowed to react for 2 hours. The reaction mixture was then poured into saturated aqueous sodium bicarbonate, more methylene chloride added, and the organic layer recovered. This was extracted with saturated aqueous sodium bicarbonate and saturated aqueous sodium chloride, dried over magnesium sulfate, and concentrated by evaporation under reduced pressure to obtain 19.34 g of orange oil. This was purified by preparative liquid chromatography eluting with a 5:95 mixture of acetone and hexane to obtain 3.95 g (27 percent of theory) of the title compound as an oil. The proton nmr spectrum was consistent with the assigned structure.

Example 15

Preparation of
(2-Hydroxyphenyl)-(2-hydroxy-3-methoxyphenyl)methane (2-Methoxymethoxyphenyl)(2-hydroxy-3-methoxyphenyl)methane (3.95 g, 14 mmol) was dissolved in 150 ml of methanol containing 0.026 g of p-toluene sulfonic acid and the mixture was heated at reflux overnight. The volatiles were then removed by evaporation under reduced pressure and the solid that remained was taken up in ether. The ethereal solution was extracted with saturated aqueous sodium bicarbonate, dried over magnesium sulfate, and concentrated by evaporation under reduced pressure. The white solid residue was dried to obtain 3.66 g (99 percent of theory) of the title compound. The proton nmr spectrum was consistent with the assigned structure.

Example 16

Preparation of
4-Methoxy-12H-dibenzo-[d,g][1,3dioxocin-6-carboxylic Acid

The procedure of Example 2 was employed starting with 3.66 g (17 mmol) of (2-hydroxyphenyl)-(2-hydroxy-3-methoxyphenyl)methane. The crude product amounted to 6.24 g and was found to contain the title compound by proton nuclear magnetic resonance. A pure sample of this compound obtained by hydrolysis of the product of Example 17 with potassium hydroxide in aqueous methanol at ambient temperature was a white solid melting at 137° C. The proton nmr spectrum was consistent with the assigned structure.

Elemental Analysis:

Calc. for $C_{16}H_{14}O_5$: % C, 67.1: % H, 4.93.
Found: % C, 66.6: % H, 4.97.

Example 17

Preparation of Methyl 4-Methoxy-12H-dibenzo[d,g][1,3]dioxocin-6-carboxylate

The procedure of Example 3 was employed starting with 6.24 g (22 mmol) of 4-methoxy-12H-dibenzo[d,g][1,3]dioxocin-6-carboxylic acid from Example 16. The product was purified by preparative liquid chromatography eluting with a 10:90 mixture of acetone and hexane. It was a light yellow solid melting at 112°-113° C. and amounting to 2.95 g (45 percent of theory). The proton nmr spectrum was consistent with the assigned structure.

Elemental Analysis:

Calc. for $C_{17}H_{16}O_5$: % C, 68.0; % H, 5.37.
Found: % C, 67.4: % H, 5.44.

Example 18

Preparation of 4-Hydroxy-12H-dibenzo[d,g][1,3dioxocin-6-carboxylic Acid

A slurry containing 3.3 g of 60 percent (in mineral oil) sodium hydride (82.5 mmol) in dry dimethylformamide was prepared and blanketed with nitrogen. To this was added with stirring 5.13 g (82.5 mmol) of ethanethiol in 50 ml of dimethylformamide and, after 30 min, 9.48 g (33 mmol) of methyl 4-methoxy-12H-dibenzo[d,g][1,3-]dioxocin-6-carboxylate in 75 ml of the same solvent was added and the mixture was heated to reflux with stirring for 3 hours at which time the reaction was indicated to be complete by thin layer chromatography. The mixture was allowed to cool, was acidified with 10 percent hydrochloric acid, and was extracted with ether. The ethereal solution was extracted with 5 percent sodium hydroxide twice and the combined alkaline extracts were acidified with hydrochloric acid and extracted with ether. The ethereal solution thus obtained was extracted with water, dried over magnesium sulfate, and concentrated by evaporation under reduced pressure. The residue was purified by preparative liquid chromatography eluting with a 20:80 mixture of acetone and hexane to obtain 2.32 g of the title compound as a white solid. The proton nmr spectrum was consistent with an impure sample of the assigned structure. A pure sample of this compound obtained by hydrolysis of the methyl ester (see Ex. 19) with potassium hydroxide in aqueous methanol at ambient temperature was a white solid melting at 161°-162° C. The proton nmr spectrum was consistent with the assigned structure.

Elemental Analysis:

Calc for $C_{15}H_{12}O_5$: % C, 66.2: % H, 4.44.
Found: % C, 65.9: % H, 4.33.

Example 19

Preparation of Methyl 4-Hydroxy-12H-dibenzo[d,g][1,3]dioxocin-6-carboxylate

The procedure of Example 3 was employed using 2.32 g (8.5 mmol) of 4-hydroxy-12H-dibenzo[d,g][1,3]-dioxocin-6-carboxylylic acid from Example 18. The crude product obtained was recrystallized from methylcyclohexane to obtain 1.26 g (52 percent of theory) of the title compound as a solid melting at 163°-165° C. The proton nmr spectrum was consistent with the assigned structure.

Elemental Analysis:

Calc. for $C_{16}H_{14}O_5$: % C, 67.1; % H, 4.93.
Found: % C, 67.1; % H, 5.09.

Example 20

Preparation of Methyl 4-Benzyloxy-12H-dibenzo[d,g][1,3],dioxocin-6-carboxylate

Methyl 4-hydroxy-12H-dibenzo[d,g][1,3]-dioxocin-6-carboxylate (0.75 g, 2.6 mmol) was placed in 20 ml of dimethylformamide along with 0.44 g (2.6 mmol) of benzyl bromide and 0.47 g (3.1 mmol) of potassium carbonate and the mixture was stirred at ambient temperature overnight. Water was then added and the resulting mixture was extracted with ether. The ether extract was dried over magnesium sulfate and concentrated by evaporation under reduced pressure to obtain the title compound as a solid melting at 132°-133° C. The proton nmr spectrum was consistent with the assigned structure.

Elemental Analysis:

Calc. for $C_{22}H_{18}O_5$: % C, 73.4; % H, 5.36.
Found: % C, 73.3: % H, 5.53.

The following were made in an analogous way from the same intermediate and the alkylating agents in parenthesis and found to have the assigned structures by elemental analyses and proton nmr spectra:

Methyl 4-ethoxy-12H-dibenzo[d,g][1,3]dioxocin-6-carboxylate (ethyl iodide), m.p., 58°-64° C.: and Methyl 4-cyanomethoxy-12H-dibenzo[d,g][1,3]dioxocin-6-carboxylate (bromoacetonitrile), m.p., 146°-147° C.:

Example 21

Preparation of (3-Bromo-2-methoxyphenyl)-(2-methoxyphenyl)methanol 2,6-Dibromoanisole (138.0 g, 0.51 mol) was dissolved in 750 ml of tetrahydrofuran and the solution cooled to −63° C. Butyl lithium (319 ml of 1.6 M, 0.51 mol) was added slowly with stirring and the mixture stirred at −60° C. for 4.5 hours and then 69.4 g (0.51 mol) of o-anisaldehyde in 250 ml of tetrahydrofuran was added slowly with stirring and the mixture allowed to stir cold for 1 hour. The mixture was allowed to warm to ambient temperature and was then poured into a mixture of ice and saturated aqueous ammonium chloride. The resulting mixture was extracted with ether and the ether extract dried over magnesium sulfate and then concentrated by evaporation under reduced pressure to obtain the title compound. This was purified by preparative liquid chromatography eluting with a 5:95 mixture of ethyl acetate and hexane to obtain 44.6 g (24 percent of theory) of material having a proton nmr spectrum consistent with the assigned structure.

Example 22

Preparation of Methyl 3-Methoxy-12H-dibenzo[d,g][1,3]dioxocin-12-one-6-carboxylate (2-Hydroxy-4-methoxyphenyl)(2-hydroxyphenyl)-methanone (16.1 g, 65.9 mmol), 36.5 g (258 mmol) of potassium carbonate, and 3.00 g (18 mmol) of potassium iodide were suspended in 250 ml of 2-propanol and heated with stirring. Dichloroacetic acid (6.00 ml, 72.6 mmol) was added slowly with a syringe and the mixture heated at reflux with stirring. After 48 hours another 5.00 ml of dichloroacetic acid was added and the reaction continued for another 48 hours. The mixture was then allowed to cool and was concentrated by evaporation under reduced pressure to obtain a solid residue. The residue was dissolved in 500 ml of water and the solution extracted with 200 ml of ether. The aqueous layer was then acidified with concentrated aqueous hydrochloric acid and then extracted twice with 500 ml portions of ether and once with 300 ml of ethyl acetate. The combined organic extracts were dried over magnesium sulfate, filtered, and concentrated by evaporation under reduced pressure to obtain 3-methoxy-12H-dibenzo[d,g][1,3]dioxocin-12-one-6-carboxylic acid as a semi-solid residue. The proton nmr spectrum was consistent with the assigned structure.

The unpurified acid was dissolved in 500 ml of methanol containing 15 g of Dowex TM sulfonic acid resin and the mixture was stirred overnight. The resin was removed by filtration and the volatiles removed by evaporation under reduced pressure. The residue obtained was dissolved in 600 ml of ether and the solution extracted with saturated aqueous sodium bicarbonate, dried over magnesium sulfate, filtered, and concentrated by evaporation under reduced pressure. The residue was further purified by filtration chromatography on silica gel eluting with a 20:80 mixture of ether and hexane to obtain 2.74 g (13 percent of theory) of the title compound as a pale yellow oil which crystallized on standing to a solid melting at 102°–106° C. The proton nmr spectrum was consistent with the assigned structure.

Elemental Analysis:

Calc. for $C_{17}H_{14}O_6$: % C, 65.0: % H, 4.49.
Found: % C, 64.4; % H, 4.59.

Example 23

Preparation of Methyl 3-Methoxy-12H-dibenzo[d,g][1,3]dioxocin-6-carboxylate.

Methyl 3-methoxy-12H-dibenzo[d,g][1,3]-dioxocin-12-one-6-carboxylate (1.35 g, 4.3 mmol) was combined with 35 ml of ethanol, 15 ml of ethyl acetate, 6 ml of acetic acid, and 0.70 g of 5 percent palladium on carbon catalyst and the suspension was placed on a Parr hydrogenator under 50 psi of hydrogen for 18 hours. The catalyst was removed by filtration and the filtrate was diluted with 300 ml of ether and 100 ml of water and the layers separated. The organic layer was extracted with 3–100 ml portions of water and 2–100 ml portions of saturated aqueous sodium bicarbonate and was then dried over magnesium sulfate, filtered, and concentrated by evaporation under reduced pressure. The residue was purified by preparative liquid chromatography on silica gel eluting with a 15:85 mixture of ether and hexane to obtain 0.76 g (59 percent of theory) of the title compound as a white powder melting at 93°–95° C. The proton nmr spectrum was consistent with the assigned structure.

Elemental Analysis:

Calc for $C_{17}H_{16}O_5$: % C, 68.0: % H, 5.33.
Found: % C, 67.6: % H, 5.49.

Example 24

Preparation of 3-Methoxy-12H-dibenzo-[d,g][1,3]dioxocin-6-carboxylic Acid

Methyl-3-methoxy-12H-dibenzo[d,g][1,3]-dioxocin-6-carboxylate (0.32 g, 1.07 mmol) was dissolved in 20 ml of tetrahydrofuran and 3.0 ml of 2 M sodium hydroxide was added. The mixture was stirred at ambient temperature overnight. It was then diluted with 20 ml of water and 50 ml of ether and the layers separated. The organic layer was extracted with water and the aqueous extract combined with the original aqueous layer. The resulting solution was acidified with 10 percent aqueous hydrochloric acid and then extracted with 4–25 ml portions of ether. The combined ether extracts were dried over magnesium sulfate, filtered, and concentrated by evaporation under reduced pressure to obtain the title compound as a yellow-white foamed solid amounting to 0.26 g (85 percent of theory) and melting at 149°–153° C. The proton nmr spectrum was consistent with the assigned structure.

Elemental Analysis:

Calc. for $C_{16}H_{14}O_5$: % C, 67.1; % H, 4.93.
Found: % C, 66.8; % H, 5.21.

Example 25

Postemergence Herbicidal Activity

Compounds of Formula I were dissolved in 14 ml acetone and 1 ml of dimethyl sulfoxide at one half of the most concentrated desired application concentration and the resulting solution was combined with 15 ml of an aqueous mixture containing about 20 percent isopropyl alcohol, about 2 percent At plus 411F crop oil concentrate, and about 0.04 percent Triton X-155 surfactant. Solutions containing lower concentrations were prepared by diluting this mixture with a solution containing equal parts of a mixture of the second component described above and acetone containing 3 percent dimethyl sulfoxide. The solutions of known concentration were sprayed evenly onto various greenhouse-grown plant species to obtain total coverage in approximately the 2–4 leaf stage by means of a hand sprayer. The treated plants and control plants were placed in a greenhouse and held under conditions conducive to growth. After 13 days the percentage of control compared to the untreated plants was determined visually. Representative compounds tested, application rates employed, plant species tested, and results are given in Table II. In this test an application of about 100 ppm results in an application of about 260 g/Ha.

TABLE II

POSTEMERGENCE CONTROL OF INDICATED SPECIES AT INDICATED DOSE RATES

| Cpd No. | Dose, ppm | Coffee- weed | Cockle- bur | Jimson- weed | Laminum | Morning- glory | Pigweed | Velvet- leaf | Wild Buck- wheat | Johnson- grass | Wild Oats | Yellow Foxtail | Yellow Nut- sedge |
|---|---|---|---|---|---|---|---|---|---|---|---|---|---|
| 1 | 250 | 100 | 75 | 90 | 100 | 70 | 100 | 90 | 70 | 60 | 70 | 20 | 85 |
| 2 | 250 | 90 | 99 | 99 | 99 | 70 | 99 | 80 | 80 | 70 | 70 | 20 | 70 |
| 5 | 250 | 10 | 75 | 100 | 90 | 80 | 100 | 80 | 35 | 85 | 80 | 75 | 80 |
| 6 | 125 | 90 | 50 | 85 | 100 | 75 | 95 | 90 | 75 | 80 | 55 | 60 | — |
| 10 | 500 | 95 | 85 | 95 | 95 | 75 | 85 | 90 | 35 | 85 | 80 | 70 | 75 |
| 11 | 2000 | 80 | 80 | 95 | 50 | — | 80 | 70 | 90 | — | 0 | 0 | 60 |
| 12 | 2000 | 90 | 75 | 100 | 60 | 75 | — | 75 | — | — | 0 | 0 | 80 |
| 14 | 1000 | 85 | 95 | 95 | 80 | 75 | 100 | 85 | 75 | 40 | 0 | 35 | 55 |
| 16 | 2000 | 85 | 60 | 60 | 60 | 75 | 100 | 85 | 80 | 0 | 0 | 0 | — |
| 20 | 500 | 90 | 75 | 75 | 90 | 50 | 100 | 95 | 100 | 80 | 0 | 80 | 25 |
| 21 | 2000 | 80 | 50 | 85 | 45 | 45 | 90 | 50 | 0 | 20 | 0 | 0 | — |
| 22 | 2000 | 80 | 75 | 75 | 100 | 75 | 95 | 70 | 0 | 0 | 0 | 0 | — |
| 23 | 250 | 100 | 75 | 40 | 75 | 70 | 70 | 85 | 60 | 50 | 10 | 20 | 60 |
| 24 | 250 | 100 | 75 | 85 | 100 | 85 | 100 | 100 | 85 | — | 45 | 30 | 0 |
| 30 | 2000 | 0 | 0 | 0 | 35 | 50 | 85 | 35 | 0 | 45 | 0 | 0 | 0 |
| 37 | 500 | 75 | 75 | 80 | 90 | 75 | 95 | 85 | 100 | 20 | 40 | 80 | 75 |

Example 26

Preemergence Herbicidal Activity

Compounds of Formula I were dissolved in 15 ml of acetone at one half of the most concentrated desired application concentration and the resulting solution was combined with an equal volume of water containing 0.1 percent of Tween 20 surfactant. Solutions containing lower concentrations were prepared by diluting this with additional aqueous surfactant solution. The seeds of a number of species of plants were planted in beds containing a loam agricultural soil and, after planting, predetermined amounts of the herbicide mixtures were sprayed on the soil surface and watered in to achieve the desired application rates. These and untreated control plants were then placed in a greenhouse under conditions conducive to germination and growth for a period of 14 days at which time a visual assessment was made of the reduction in stand and growth for the treated plants as compared to the control plants. Representative compounds tested, application rates employed, plant species tested, and results are given in Table III.

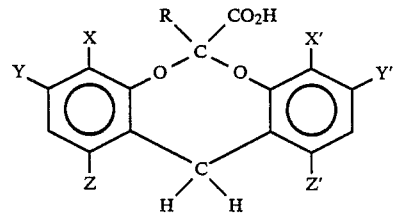

wherein
R represents H or $CH_3$ and
X, X', Y, Y', Z, and Z' each, independently represent H, F, Cl, Br, I, CN, $NO_2$, $CO_2H$, $NH_2$, $C_1$-$C_4$ alkyl, $C_1$-$C_4$ alkoxy, $C_1$-$C_4$ alkylthio, C1-C4 mono- or dialkylamino, ($C_1$-$C_3$ alkyl)carbonyl or phenylcarbonyl, wherein each alkyl, alkoxy, and alkylthio group is optionally substituted with one or more groups selected from $C_1$-$C_4$ alkoxy, $C_1$-$C_4$ alkylthio, F, Cl, Br, CN and phenyl and wherein each phenyl group is optionally substituted with up to 3 groups selected from F, Cl, Br, CN, $CF_3$, $C_1$-$C_4$ alkyl, and $C_1$-$C_4$ alkoxy; with the provisos that X,

TABLE III

PREEMERGENCE CONTROL OF INDICATED SPECIES AT INDICATED DOSE RATES

| Cpd No. | Dose, lb/A | Curly Dock | Jimson Weed | Morning glory | Pig- weed | Velvet- leaf | Cheat Grass | Johnson- grass | Yellow Foxtail | Yellow Nut- sedge |
|---|---|---|---|---|---|---|---|---|---|---|
| 1 | 2.0 | 100 | 100 | 50 | 100 | 90 | 100 | 95 | 40 | 100 |
| 2 | 0.5 | 75 | 100 | 100 | 50 | 100 | 100 | 75 | 0 | 90 |
| 6 | 1.0 | 90 | 90 | 85 | 90 | 90 | 90 | 90 | 85 | 100 |
| 10 | 1.0 | 90 | 80 | 35 | 90 | 90 | 85 | 88 | 65 | 100 |
| 13 | 4.0 | 90 | 100 | 100 | 0 | 0 | 0 | 100 | 0 | 40 |
| 19 | 4.0 | 90 | 45 | 40 | 95 | 95 | 10 | 10 | 15 | 0 |
| 20 | 4.0 | 90 | 100 | 25 | 80 | 80 | 0 | 0 | 0 | 90 |
| 18 | 4.0 | — | 0 | 75 | 100 | 100 | 50 | 50 | 0 | 85 |
| 24 | 4.0 | 55 | 0 | 0 | 100 | 0 | 0 | 0 | 0 | — |
| 26 | 4.0 | 70 | 50 | 25 | 90 | 80 | 100 | 60 | 50 | 100 |

Y, Z, X', Y', and Z' do not all represent H and that X and X', Y and Y', and Z and Z' are not simultaneously the same: or an agriculturally acceptable salt, ester, or amide thereof.

2. A compound according to claim 1 wherein X', Y', and Z' each represent hydrogen.

What is claimed is:

1. A substituted dibenzo[d,g][1,3]dioxocin-6-carboxylic acid compound of the formula 3. A compound according to claim 1 wherein X, X', Y, Y', Z, and Z' are selected from H, F, Cl, Br, $CH_3$, $OCH_3$, $SCH_3$, $CF_3$, or $OC_5H_6$.

4. A compound according to claim 1 wherein at least one of X and X' represents a designated substituent other than hydrogen.

5. A compound according to claim 1 wherein R represents hydrogen.

6. A compound according to claim 1 wherein the compound is in the form of an agriculturally acceptable salt, ester, or amide.

7. A compound according to claim 6 wherein the compound is in the form of an agriculturally acceptable ester.

8. A compound according to claim 7 wherein the ester is a $C_1$–$C_8$ alkyl or $C_3$–$C_8$ alkenyl ester, each substituted with up to 3 groups selected from $C_1$–$C_4$ alkoxy, F, Cl, Br, and phenyl, or a phenyl ester optionally substituted with up to 3 groups selected from F, Cl, Br, $CH_3$, or $CF_3$.

9. A compound according to claim 8 wherein the ester is a $C_1$–$C_4$ alkyl ester.

10. A compound according to claim 9 wherein the ester is a methyl ester.

11. A compound according to claim 6 wherein the compound is in the form of an agriculturally acceptable salt.

12. A compound according to claim 3 wherein the compound is 4-chloro-12H-dibenzo[d,g][1,3]dioxocin-6-carboxylic acid or an agriculturally acceptable salt, ester, or amide thereof.

13. A compound according to claim 3 wherein the compound is 4-methyl-12H-dibenzo[d,g][1,3]dioxocin-6-carboxylic acid or an agriculturally acceptable salt, ester, or amide thereof.

14. A compound according to claim 3 wherein the compound is 4-methoxy-12H-dibenzo[d,g][1,3]dioxocin-6-carboxylic acid or an agriculturally acceptable salt, ester, or amide thereof.

15. A composition useful for controlling undesirable vegetation which comprises in admixture with an agriculturally acceptable adjuvant or carrier an herbicidally effective amount of a substituted dibenzo[d,g][1,3]dioxocin-6-carboxylic acid compound of the formula

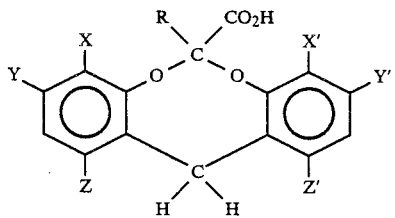

wherein
R represents H or $CH_3$ and
X, X', Y, Y', Z, and Z' each, independently represent H, F, Cl, Br, I, CN, $NO_2$, $CO_2H$, $NH_2$, $C_1$–$C_4$ alkyl, $C_1$–$C_4$ alkoxy, $C_1$–$C_4$ alkylthio, $C_1$–$C_4$ mono- or dialkylamino, ($C_1$–$C_3$ alkyl)carbonyl, or phenylcarbonyl, wherein each alkyl, alkoxy, and alkylthio group is optionally substituted with one or more compatible groups selected from $C_1$–$C_4$ alkoxy, $C_1$–$C_4$ alkylthio, F, Cl, Br, CN and phenyl and wherein each phenyl group is optionally substituted with up to 3 groups selected from F, Cl, Br, CN, $CF_3$, $C_1$–$C_4$ alkyl, and $C_1$–$C_4$ alkoxy: with the proviso that X, Y, Z, X', Y', and Z' do not all represent H; or an agriculturally acceptable salt, ester, or amide thereof.

16. A composition according to claim 15 wherein X', Y', and Z' each represent hydrogen.

17. A composition according to claim 15 wherein X, X', Y, Y', Z, and Z' each independently represent H, F, Cl, Br, $CH_3$, $OCH_3$, $SCH_3$, $CF_3$, or $OC_6H_5$.

18. A composition according to claim 15 wherein at least one of X and X' represents a designated substituent other than hydrogen.

19. A composition according to claim 15 wherein R represents hydrogen.

20. A composition according to claim 15 wherein the compound is in the form of an agriculturally acceptable salt, ester, or amide.

21. A composition according to claim 20 wherein the compound is in the form of an agriculturally acceptable ester.

22. A composition according to claim 21 wherein the ester is a $C_1$–$C_8$ alkyl or $C_3$–$C_8$ alkenyl ester, each substituted with up to 3 compatible groups selected from $C_1$–$C_4$ alkoxy, F, Cl, Br, and phenyl, or a phenyl ester optionally substituted with up to 3 groups selected from F, Cl, Br, $CH_3$, or $CF_3$.

23. A composition according to claim 22 wherein the ester is a $C_1$–$C_4$ alkyl ester.

24. A composition according to claim 23 wherein the ester is a methyl ester.

25. A composition according to claim 20 wherein the compound is in the form of an agriculturally acceptable salt.

26. A composition according to claim 17 wherein the compound is 4-chloro-12H-dibenzo[d,g][1,3]-dioxocin-6-carboxylic acid or an agriculturally acceptable salt, ester, or amide thereof.

27. A composition according to claim 17 wherein the compound is 4-methyl-12H-dibenzo[d,g][1,3]-dioxocin-6-carboxylic acid or an agriculturally acceptable salt, ester, or amide thereof.

28. A composition according to claim 17 wherein the compound is 4-methoxy-12H-dibenzo[d,g][1,3]-dioxocin-6-carboxylic acid or an agriculturally acceptable salt, ester, or amide thereof.

* * * * *